United States Patent
Barbour

(10) Patent No.: US 11,237,176 B2
(45) Date of Patent: Feb. 1, 2022

(54) INFRARED ASSAY DETECTING SECONDARY STRUCTURE PROFILES OF ALPHA-SYNUCLEIN

(71) Applicant: PROTHENA BIOSCIENCES LIMITED, Dublin (IE)

(72) Inventor: Robin Barbour, Walnut Creek, CA (US)

(73) Assignee: PROTHENA BIOSCIENCES LIMITED, Dublin (IE)

(*) Notice: Subject to any disclaimer, the term of this patent is extended or adjusted under 35 U.S.C. 154(b) by 0 days.

(21) Appl. No.: 16/346,841

(22) PCT Filed: Dec. 1, 2017

(86) PCT No.: PCT/US2017/064332
§ 371 (c)(1),
(2) Date: May 1, 2019

(87) PCT Pub. No.: WO2018/102763
PCT Pub. Date: Jun. 7, 2018

(65) Prior Publication Data
US 2019/0277863 A1    Sep. 12, 2019

Related U.S. Application Data

(60) Provisional application No. 62/429,604, filed on Dec. 2, 2016.

(51) Int. Cl.
*G01N 33/68* (2006.01)
*C07K 16/18* (2006.01)
*G01N 21/3577* (2014.01)
*G01N 21/552* (2014.01)
*A61P 25/16* (2006.01)

(52) U.S. Cl.
CPC .......... *G01N 33/6896* (2013.01); *A61P 25/16* (2018.01); *C07K 16/18* (2013.01); *G01N 21/3577* (2013.01); *G01N 21/552* (2013.01); *C07K 2317/34* (2013.01); *G01N 2333/46* (2013.01)

(58) Field of Classification Search
CPC .......... G01N 33/6896; G01N 21/3577; G01N 21/552; G01N 2333/46; G01N 2333/4709; G01N 2800/2835; A61P 25/16; C07K 16/18; C07K 2317/34
See application file for complete search history.

(56) References Cited

U.S. PATENT DOCUMENTS

| | | | |
|---|---|---|---|
| 7,910,333 B2 * | 3/2011 | Chilcote | C07K 16/18 435/69.7 |
| 9,605,056 B2 * | 3/2017 | Barbour | A61P 25/00 |
| 2015/0259404 A1 | 9/2015 | Barbour et al. | |
| 2016/0231335 A1 | 8/2016 | Nagele | |

FOREIGN PATENT DOCUMENTS

| | | | |
|---|---|---|---|
| WO | WO/2005/047860 | * | 5/2005 |
| WO | WO 2013/063516 A1 | | 5/2013 |
| WO | WO 2013/112945 A1 | | 8/2013 |
| WO | WO 2014/058924 A9 | | 4/2014 |
| WO | WO 2015/121339 A1 | | 8/2015 |
| WO | WO 2017/033152 A1 | | 3/2017 |
| WO | WO 2018/007979 A1 | | 1/2018 |
| WO | WO 2018/102763 A1 | | 6/2018 |

OTHER PUBLICATIONS

Ramakrishnan et al., Biochemistry, vol. 45, No. 10, 2006 (Year: 2006).*
Lindstrom et al., Immunotherapy, 6(2):141-153, 2014 (Year: 2014).*
Etezadi et al., Light: Science & Applications (2017) 6, e17029. (Year: 2017).*
PCT/US2017/064332 International Search Report and Written Opinion dated Dec. 1, 2017.
Elfrink, et al., "Structural changes of membrane-anchored native $PrP_c$," PNAS, vol. 105, No. 31, pp. 10815-10819, (Aug. 5, 2008).
Nabers, et al., "Amyloid-β-Secondary Structure Distribution in Cerebrospinal Fluid and Blood Measured by an Immuno-Infrared-Sensor: A Biomarker Candidate for Alzheimer's Disease," Anal. Chem. 88, pp. 2755-2762, (2016).
PCT/US2017/064332 International Preliminary Report on Patentability dated Jun. 4, 2019.
Llorens, et al., "Evaluation of α-synuclein a a novel cerebrospinal fluid biommarker in different forms of prion diseases," Alzheimer's & Dementia, 13, 710-719, (2017).
EP 17876624 Extended European Search Report dated May 29, 2020.

* cited by examiner

*Primary Examiner* — Kimberly Ballard
*Assistant Examiner* — Stacey N Macfarlane
(74) *Attorney, Agent, or Firm* — Alston & Bird LLP

(57) ABSTRACT

The invention provides an infrared assay which allows the secondary structure analysis of alpha-synuclein from complex fluids like serum, blood plasma or cerebrospinal fluid without prior isolation, concentration or pretreatment. The secondary structure profile provides an indication of the proportion of alpha-synuclein in aggregated form and/or extent of aggregation of alpha-synuclein in aggregated form.

26 Claims, 3 Drawing Sheets
Specification includes a Sequence Listing.

SEQUENCE LISTING

<160> NUMBER OF SEQ ID NOS: 17

<210> SEQ ID NO 1
<211> LENGTH: 140
<212> TYPE: PRT
<213> ORGANISM: Homo sapiens

<400> SEQUENCE: 1

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140

<210> SEQ ID NO 2
<211> LENGTH: 115
<212> TYPE: PRT
<213> ORGANISM: Artificial Sequence
<220> FEATURE:
<223> OTHER INFORMATION: Synthesized

<400> SEQUENCE: 2

Val Gln Leu Gln Gln Ser Gly Pro Glu Leu Val Lys Pro Gly Thr Ser
1               5                   10                  15

Val Lys Ile Ser Cys Lys Ala Ser Gly Tyr Ser Phe Thr Ser Tyr Tyr
            20                  25                  30

Ile His Trp Val Lys Gln Ser Pro Gly Gln Gly Leu Glu Trp Ile Gly
        35                  40                  45

Trp Ile Tyr Pro Gly Ser Gly Asn Thr Lys Tyr Ser Glu Lys Phe Lys
    50                  55                  60

Gly Lys Ala Thr Leu Thr Ala Asp Thr Ser Ser Ser Thr Ala Tyr Met
65                  70                  75                  80

Gln Leu Ser Ser Leu Thr Ser Glu Asp Ser Ala Val Tyr Phe Cys Ala
                85                  90                  95

Arg Asp Gly Cys Tyr Gly Phe Ala Tyr Trp Gly Gln Gly Thr Leu Val
            100                 105                 110

Thr Val Ser
    115

<210> SEQ ID NO 3
<211> LENGTH: 111
<212> TYPE: PRT
<213> ORGANISM: Artificial Sequence
<220> FEATURE:
<223> OTHER INFORMATION: Synthesized -continued

```
<400> SEQUENCE: 3

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Phe Leu Ile Cys Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Phe Thr Phe Gly Ser Gly Thr Lys Leu Glu Ile Lys
            100                 105                 110

<210> SEQ ID NO 4
<211> LENGTH: 5
<212> TYPE: PRT
<213> ORGANISM: Artificial Sequence
<220> FEATURE:
<223> OTHER INFORMATION: Synthesized

<400> SEQUENCE: 4

Ser Tyr Tyr Ile His
1               5

<210> SEQ ID NO 5
<211> LENGTH: 17
<212> TYPE: PRT
<213> ORGANISM: Artificial Sequence
<220> FEATURE:
<223> OTHER INFORMATION: Synthesized

<400> SEQUENCE: 5

Trp Ile Tyr Pro Gly Ser Gly Asn Thr Lys Tyr Ser Glu Lys Phe Lys
1               5                   10                  15

Gly

<210> SEQ ID NO 6
<211> LENGTH: 8
<212> TYPE: PRT
<213> ORGANISM: Artificial Sequence
<220> FEATURE:
<223> OTHER INFORMATION: Synthesized

<400> SEQUENCE: 6

Asp Gly Cys Tyr Gly Phe Ala Tyr
1               5

<210> SEQ ID NO 7
<211> LENGTH: 15
<212> TYPE: PRT
<213> ORGANISM: Artificial Sequence
<220> FEATURE:
<223> OTHER INFORMATION: Synthesized

<400> SEQUENCE: 7

Lys Ala Ser Gln Ser Val Asp Tyr Asp Gly Asp Ser Tyr Met Asn
1               5                   10                  15

<210> SEQ ID NO 8
```

```
<211> LENGTH: 7
<212> TYPE: PRT
<213> ORGANISM: Artificial Sequence
<220> FEATURE:
<223> OTHER INFORMATION: Synthesized

<400> SEQUENCE: 8

Ala Ala Ser Asn Leu Glu Ser
1               5

<210> SEQ ID NO 9
<211> LENGTH: 9
<212> TYPE: PRT
<213> ORGANISM: Artificial Sequence
<220> FEATURE:
<223> OTHER INFORMATION: Synthesized

<400> SEQUENCE: 9

Gln Gln Ser Asn Glu Asp Pro Phe Thr
1               5

<210> SEQ ID NO 10
<211> LENGTH: 113
<212> TYPE: PRT
<213> ORGANISM: Artificial sequence
<220> FEATURE:
<223> OTHER INFORMATION: Synthesized

<400> SEQUENCE: 10

Glu Val Asn Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asn Asp
            20                  25                  30

Tyr Met Ala Trp Val Arg Gln Thr Pro Glu Lys Arg Leu Asp Trp Val
        35                  40                  45

Ala Ser Ile Ser Ser Gly Gly Asp Tyr Ile Tyr Ala Asp Asn Val
    50                  55                  60

Lys Gly Arg Phe Thr Ile Ser Arg Asp Asn Ala Lys His Thr Leu Tyr
65                  70                  75                  80

Leu Gln Met Ser Ser Leu Lys Ser Glu Asp Thr Ala Ile Tyr Tyr Cys
                85                  90                  95

Ser Asn Leu Phe Asp Tyr Trp Gly Gln Gly Thr Thr Leu Thr Val Ser
            100                 105                 110

Ser

<210> SEQ ID NO 11
<211> LENGTH: 112
<212> TYPE: PRT
<213> ORGANISM: Artificial sequence
<220> FEATURE:
<223> OTHER INFORMATION: Synthesized

<400> SEQUENCE: 11

Asp Ile Val Ile Thr Gln Asp Glu Leu Ser Asp Pro Val Thr Ser Gly
1               5                   10                  15

Glu Ser Val Ser Ile Ser Cys Arg Ser Asn Lys Ser Leu Leu Tyr Lys
            20                  25                  30

Asp Gly Lys Thr Tyr Leu Asn Trp Phe Leu Gln Arg Pro Gly Gln Ser
        35                  40                  45

Pro Gln Leu Leu Ile Tyr Leu Met Ser Thr Arg Ala Ser Gly Val Ser
    50                  55                  60
```

-continued

```
Asp Arg Phe Ser Gly Ser Gly Ser Gly Thr Asp Phe Thr Leu Glu Ile
 65                  70                  75                  80

Ser Arg Val Lys Ala Glu Asp Val Gly Val Tyr Tyr Cys Leu Gln Leu
                 85                  90                  95

Leu Glu Phe Pro Leu Thr Phe Gly Ala Gly Thr Lys Leu Glu Leu Lys
            100                 105                 110
```

<210> SEQ ID NO 12
<211> LENGTH: 5
<212> TYPE: PRT
<213> ORGANISM: Artificial sequence
<220> FEATURE:
<223> OTHER INFORMATION: Synthesized

<400> SEQUENCE: 12

```
Asn Asp Tyr Met Ala
 1               5
```

<210> SEQ ID NO 13
<211> LENGTH: 10
<212> TYPE: PRT
<213> ORGANISM: Artificial sequence
<220> FEATURE:
<223> OTHER INFORMATION: Synthesized

<400> SEQUENCE: 13

```
Gly Phe Thr Phe Ser Asn Asp Tyr Met Ala
 1               5                  10
```

<210> SEQ ID NO 14
<211> LENGTH: 4
<212> TYPE: PRT
<213> ORGANISM: Artificial sequence
<220> FEATURE:
<223> OTHER INFORMATION: Synthesized

<400> SEQUENCE: 14

```
Leu Phe Asp Tyr
 1
```

<210> SEQ ID NO 15
<211> LENGTH: 16
<212> TYPE: PRT
<213> ORGANISM: Artificial sequence
<220> FEATURE:
<223> OTHER INFORMATION: Synthesized

<400> SEQUENCE: 15

```
Arg Ser Asn Lys Ser Leu Leu Tyr Lys Asp Gly Lys Thr Tyr Leu Asn
 1               5                  10                  15
```

<210> SEQ ID NO 16
<211> LENGTH: 7
<212> TYPE: PRT
<213> ORGANISM: Artificial sequence
<220> FEATURE:
<223> OTHER INFORMATION: Synthesized

<400> SEQUENCE: 16

```
Leu Met Ser Thr Arg Ala Ser
 1               5
```

<210> SEQ ID NO 17
<211> LENGTH: 9
<212> TYPE: PRT
<213> ORGANISM: Artificial sequence

```
<220> FEATURE:
<223> OTHER INFORMATION: Synthesized

<400> SEQUENCE: 17

Leu Gln Leu Leu Glu Phe Pro Leu Thr
1               5
```

INFRARED ASSAY DETECTING SECONDARY STRUCTURE PROFILES OF ALPHA-SYNUCLEIN

CROSS REFERENCE TO RELATED APPLICATIONS

This application is a U.S. National Stage Entry of PCT/US2017/064332 filed Dec. 1, 2017, which claims the benefit of U.S. Provisional Patent Application No. 62/429,604, filed Dec. 2, 2016, which is incorporated by reference in its entirety for all purposes.

REFERENCE TO A SEQUENCE LISTING

This application includes an electronic sequence listing in a file named 525531SEQLIST.TXT, created on May 1, 2019, and containing 8,830,622 bytes, which is incorporated by reference.

BACKGROUND

Alpha-synuclein brain pathology is a conspicuous feature of several neurodegenerative diseases termed synucleinopathies. Alpha-synuclein is the main component of Lewy bodies (LBs) and Lewy neurites, which are intraneuronal inclusions.

Synucleinopathies include Parkinson's disease (PD), dementia with Lewy bodies (DLB), the Lewy body variant of Alzheimer's disease (LBVAD), diffuse Lewy body disease (DLBD), multiple systems atrophy (MSA), and neurodegeneration with brain iron accumulation type-1 (NBIA-1).

Synucleinopathies are a common cause for movement disorders and cognitive deterioration in the aging population (Galasko et al., Arch. Neurol. (1994) 51:888-95). To date these disorders are neither curable nor preventable and understanding the causes and pathogenesis of PD is critical towards developing new treatments (Tanner et al., Curr. Opin. Neurol. (2000) 13:427-30). The cause for PD is controversial and multiple factors have been proposed to play a role, including various neurotoxins and genetic susceptibility factors.

Several studies have shown that alpha-synuclein plays a central role in PD pathogenesis because: (1) this protein accumulates in LBs (Spillantini et al., Nature (1997) 388: 839-40; Takeda et al., J. Pathol. (1998) 152:367-72; Wakabayashi et al., Neurosci. Lett. (1997) 239:45-8), (2) mutations in the alpha-synuclein gene co-segregate with rare familial forms of Parkinsonism (Kruger et al., Nature Gen. (1998) 18:106-8; Polymeropoulos et al., Science (1997) 276:2045-7) and, (3) its overexpression in transgenic mice (Masliah et al., Science (2000) 287:1265-9) and *Drosophila* (Feany et al., Nature (2000) 404:394-8) mimics several pathological aspects of PD. Thus, the fact that accumulation of alpha-synuclein in the brain is associated with similar morphological and neurological alterations in species as diverse as humans, mice, and flies suggests that this molecule contributes to the development of PD.

LBs were consistently found to contain a large amount of accumulated alpha-synuclein (Spillantini et al. National Acad Sciences 95: 6469-6473 (1998)). Analysis of abnormally processed and aggregated alpha-synuclein from patients have revealed different posttranslational modifications, including phosphorylation, nitration, ubiquitination and C-terminal truncation of the protein (Giasson et al. Science 290: 985-989 (2000); Baba et al. Am J Pathol. 152: 879-884 (1998); Fujiwara et al. Nat Cell Biol. 4: 160-164 (2002)).

Alpha-synuclein and other biomarkers can be detected in body fluids by techniques such as enzyme-linked immunesorbent assays (ELISA), surface plasmon resonance spectroscopy (SPR), surface fluorescence intensity distribution analysis (sFIDA) or mass spectroscopy. These techniques usually do not provide direct information about the secondary structure of the analytes. Even when antibody based methods like ELISA or SPR are performed with a conformationally sensitive antibody, they provide information about only one conformation (I. Morgado et al., Proc. Natl. Acad. Sci., 109(31): 12503-12508 (2012); Venkataramani et al., JAD 29(2):361-371 (2012)).

Purified proteins have been analyzed by Fourier-transform infrared (FTIR-) spectroscopy or attenuated total reflection (ATR-) sensor surfaces has been described (J. Ollesch et al., Appl. Spectrosc., 61(10):1025-1031 (2007); K. Elfrink, J. Ollesch et al., Proc Natl Acad Sci, 105(31): 10815-10819 (2008); Frost et al., J. Biol. Chem., 284(6): 3546-3551 (2009); S. Funke et al., J. Biol. Chem., 280(10): 8912-7 (2005)). Recently, infrared attenuated total reflection spectroscopy has been reported for analysis of amyloid beta and related proteins in biological fluids (WO 2015/121339; Nabers et al., Analytical Chemistry, 88: 2755-2762 (2016)). The accuracy of this technique in analyzing second structure of peptides potentially transitioning between several conformational states is, however, dependent on provision of a capture antibody whose binding is at least largely independent of conformation state of a peptide.

SUMMARY OF THE CLAIMED INVENTION

The invention provides a method for determining a profile of secondary structure of alpha-synuclein in a sample, comprising (a) introducing the sample into a cell comprising an infrared source, an infrared sensor element linked to an antibody to within residues 40-55 or 91-97 of alpha-synuclein, and an infrared detector, whereby alpha-synuclein in the sample binds to the antibody on the surface of the infrared sensor element; (b) submitting an infrared beam from the infrared source through the infrared sensor to the infrared detector to obtain an infrared spectrum characterizing the alpha-synuclein of the sample; and (c) analyzing the obtained infrared spectrum to determine a secondary structure profile of the alpha-synuclein in the sample. Optionally, the secondary structure profile provides an indication of the proportion of alpha-synuclein in aggregated form and/or extent of aggregation of alpha-synuclein in aggregated form.

Optionally, step (c) of the method for determining a profile of secondary structure of alpha-synuclein comprises analyzing the shift of an amide I band maximum of alpha-synuclein to determine the secondary structure of alpha-synuclein, an amide I band maximum frequency of 1646 $cm^{-1}$ indicating monomeric alpha-synuclein and a lower amide I band maximum frequency of alpha-synuclein indicating aggregated alpha-synuclein. Optionally, step (c) comprises comparing the obtained infrared spectrum with a spectrum of alpha-synuclein with a known secondary structure and/or with a known concentration.

Optionally, the infrared sensor element comprises a germanium internal reflection element of trapezoid or parallelogram shape transparent in the infrared with sufficient signal to noise ratio to detect an amide I band. Optionally, the antibodies are linked to the infrared sensor by silane or thiol linkers. Optionally, the antibody is 23E8 (ATCC Accession No. PTA-122711), or an antibody having the CDRs of 23E8. Optionally, the antibody is 1H7 (ATCC Accession No. PTA-8220) or an antibody having the CDRs of 1H7. Optionally, the antibody is MJFR1 (a rabbit monoclonal antibody to alpha-synuclein commercially available at ABCAM®) or an antibody having the CDRs of MJFR1.

Optionally, the method for determining a profile of secondary structure of alpha-synuclein in a sample further comprises: (i) detecting a signal, parallel to the infrared analysis, by another optical method, including UV/Vis-fluorescence, at different wavelengths; and/or (ii) combining immuno-ATR-IR vibrational spectroscopy with parallel fluorescence spectroscopy.

Optionally, the sample is from a subject. Optionally, the sample is from a human. Optionally, the sample is from a transgenic mouse with a transgene expressing human alpha-synuclein. Optionally, the sample is a body fluid. Optionally, the sample is cerebrospinal fluid (CSF) or blood of a human. Optionally, the human has a Lewy body disease. Optionally, the human has Parkinson's disease. Optionally, the human is receiving immunotherapy for the disease. Optionally, the sample is a brain homogenate of a human or transgenic animal. Optionally, the sample is a medium used to culture cells. Optionally, the cells express recombinant human alpha-synuclein. Optionally, the method of the invention is performed multiple times on samples from the same subject to detect changes in profile over time. Optionally, the human is receiving a regime of immunotherapy and the regime changes in response to changes in the profile over time.

Optionally, the sample is from a patient with Parkinson's disease, and the amide I band maximum frequency of the sample occurs below 1646 $cm^{-1}$ indicating aggregated alpha-synuclein. Optionally, the patient has prodromal Parkinson's disease. Optionally, the patient has mild Parkinson's disease. Optionally, the patient has moderate Parkinson's disease. Optionally, the patient has advanced Parkinson's disease.

Optionally, the method of the invention is performed on a population of subjects, wherein a greater proportion of subjects with a level of the amide I band maximum frequency of alpha-synuclein below a threshold receive treatment for Parkinson's disease than subjects in which the level of the amide I band maximum frequency of alpha-synuclein is above the threshold. Optionally, the threshold of the amide I band maximum frequency is 1643 $cm^{-1}$.

DEFINITIONS

Figure 1A:
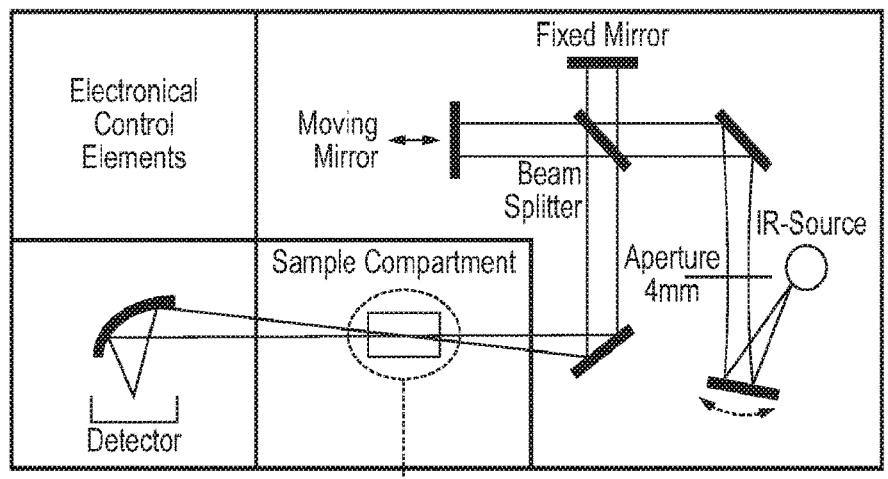
FIGS. 1A-C: Schematic view of the sensoric device in the sample chamber of an IR spectrometer (A), detailed view on the sample chamber (B), and schematics of the flow through cuvette (C).

The phrase that an antibody "specifically binds" to a target refers to a binding reaction which is determinative of the presence of the antibody in the presence of a heterogeneous population of other biologics. Thus, under designated immunoassay conditions, a specified molecule binds preferentially to a particular target and does not bind in a significant amount to other biologics present in the sample. Specific binding of an antibody to a target under such conditions requires the antibody be selected for its specificity to the target. Specific binding between two entities means an affinity of at least $10^6$, $10^7$, $10^8$, $10^9$ or $10^{10}$ $M^{-1}$. Affinities greater than $10^8$ $M^{-1}$ are preferred. Lack of specific binding means binding to a target indistinguishable from an irrelevant control antibody and/or an affinity of less than $10^6 M^{-1}$.

The term "antibody" includes intact antibodies and binding fragments thereof. Typically, fragments compete with the intact antibody from which they were derived for specific binding to an antigen fragment including separate heavy chains, light chains Fab, Fab' F(ab')2, Fabc, and Fv. Fragments are produced by recombinant DNA techniques, or by enzymatic or chemical separation of intact immunoglobulins. The term "antibody" also includes one or more immunoglobulin chains that are chemically conjugated to, or expressed as, fusion proteins with other proteins. The term "antibody" also includes bispecific antibody. A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, Clin. Exp. Immunol. 79:315-321 (1990); Kostelny et al., J. Immunol. 148, 1547-1553 (1992).

Antibodies of the invention are typically substantially pure from undesired contaminant. This means that an agent is typically at least about 50% w/w (weight/weight) purity, as well as being substantially free from interfering proteins and contaminants. Sometimes the antibodies are at least about 80% w/w and, more preferably at least 90 or about 95% w/w purity. However, using conventional protein purification techniques, homogeneous antibodies of at least 99% w/w can be obtained.

The term "epitope" or "antigenic determinant" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids or post-translationally modified amino acids are typically retained on exposure to denaturing solvents whereas epitopes formed by tertiary folding are typically lost on treatment with denaturing solvents. An epitope typically includes at least 3, but generally speaking 5-10 amino acids in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed. (1996). Antibodies that recognize the same epitope can be identified in a simple immunoassay showing the ability of one antibody to block the binding of another antibody to a target antigen.

The term "body fluid" refers to those fluids of a mammalian host which is suspected contain measurable amounts of alpha-synuclein or fragments thereof, specifically including blood, cerebrospinal fluid (CSF), brain or any other organ interstitial fluid (ISF), urine, saliva, aqueous humour, and peritoneal fluid. The term "blood" refers to whole blood, as well as blood plasma and serum.

A synucleinopathic disease means a disease characterized by Lewy bodies, Lewy neurites or other deposits of alpha-synuclein.

Monomeric alpha-synuclein is believed to aggregate in stages first forming soluble oligomers and then insoluble fibrils, which form Lewy bodies. Aggregated alpha-synuclein refers to alpha-synuclein in any degree of aggregated state including dimers up to complex three dimensional structures, such as Lewy bodies. Fibrillar alpha-synuclein is rich in β-sheets as compared to α-helices in oligomeric alpha-synuclein. When alpha-synuclein transitions from a monomeric form to an aggregated form, such as in subjects with Lewy bodies, the overall secondary structure distribution shifts mostly from a random conformation through α-helices toward β-sheets. The maximum absorbance value of an amide I band resulting from vibrational stretching of carbonyl groups in the alpha-synuclein backbone shifts correspondingly shifts to a lower wavelength as aggregation of alpha-synuclein increases.

Qualitative assay detects presence or absence of an analyte. A quantitative assay detects not only presence or absence of the analyte but if present provides an absolute or relative amount of the analyte.

Compositions or methods "comprising" one or more recited elements may include other elements not specifically recited. For example, a composition that comprises alpha-synuclein peptide encompasses both an isolated alpha-synuclein peptide and alpha-synuclein peptide as a component of a larger polypeptide sequence.

A sample refers to a test aliquot that may contain alpha-synuclein in aggregated form. Such samples can be obtained from patients, cell cultures or transgenic animals, among other sources as discussed further below. A sample can be subject to further processing before analysis, such as the removal of irrelevant components, or addition of solvents, buffers and so forth.

DETAILED DESCRIPTION

The present invention provides an immuno infrared assay for analyzing the conformational state of alpha-synuclein using antibodies against alpha-synuclein that can capture alpha-synuclein in various states of aggregation. These antibodies bind to epitopes within residues 40-55 or 91-97 of alpha-synuclein. Such antibodies are immobilized on a sensor element, such that the antibodies can capture alpha-synuclein from a sample on the surface of the sensor. Infrared radiation is passed through the sensor element and emerging radiation is detected. The spectrum of radiation emerging from the sensor element depends on the conformational state of aggregation. More specifically the maximum absorbance value of an amide I band resulting from vibrational stretching of carbonyl groups in the alpha-synuclein backbone shifts to a lower wavelength as aggregation of alpha-synuclein increases. Thus, the detected spectrum can provide a measure of the extent of aggregation and/or amount of aggregated alpha-synuclein in a sample. The extent and/or amount of alpha-synuclein is useful for assisting in diagnosis of synucleinopathic disease or susceptibility thereto and for measuring the status of subjects with synucleinopathic disease and their responses to treatment.

I) Antibodies Used in Detection

The invention provides three classes of antibody for use in capturing alpha-synuclein in the disclosed assay methods. The antibodies can be used alone or in combination with one another or in combination with other antibodies. In some methods, one of the three classes of antibodies disclosed below is used alone as the capture antibody. The three classes of antibody described below have a different epitope specificity than the 4B12 antibody (residues 103-108 of alpha-synuclein reported by WO2015121339).

The first class of capture antibody specifically binds to an epitope within residues 40-55 of alpha-synuclein. The 23E8 antibody or an antibody having the variable regions or CDRs of 23E8 (preferably as defined by Kabat) is an example of such an antibody. A hybridoma producing the 23E8 antibody has been deposited as ATCC Accession No. PTA-122711. Mature heavy and light chain variable regions are designated SEQ ID NOs:10 and 11. CDRs H1, H2 and H3 by Kabat are designated SEQ ID NOs:12-14 and CDRs L1, L2 and L3 by Kabat are designated SEQ ID NOs:15-17.

The second class of antibody specifically binds to an epitope within residues 91-97 of alpha-synuclein. The 1H7 antibody or an antibody having the variable regions or CDRs of 1H7 (preferably as defined by Kabat) is an example of such an antibody for use on the surface of the infrared sensor element. A hybridoma producing the 1H7 antibody has been deposited as ATCC Accession No. PTA-8220. Mature heavy and light chain variable regions are designated SEQ ID NOs:9 and 11 of US 20150024433 (present SEQ ID NOs:2 and 3). CDRs H1, H2 and H3 by Kabat are designated SEQ ID NOs:12-14 (present SEQ ID NOs:4-6) and CDRs L1, L2 and L3 by Kabat are designated SEQ ID NOs:15-17 of US 20150024433 (present SEQ ID NOs:7-9).

The third class of antibody specifically binds to an epitope within residues 118-123 of alpha-synuclein. The MJFR1 antibody (a rabbit monoclonal antibody) or an antibody having the CDRs of MJFR1 (preferably as defined by Kabat) is an example of such an antibody for use on the surface of the infrared sensor element. The MJFR1 antibody is commercially available from ABCAM®.

When an antibody is said to bind to an epitope within specified residues, such as alpha-synuclein 40-55, for example, what is meant is that the antibody specifically binds to a polypeptide consisting of the specified residues (i.e., alpha-synuclein 40-55 in this an example). Such an antibody does not necessarily contact every residue within alpha-synuclein 40-55. Nor does every single amino acid substitution or deletion within alpha-synuclein 40-55 necessarily significantly affect binding affinity. Epitope specificity of an antibody can be determined, for example, by testing a collection of overlapping peptides of about 15 amino acids spanning the sequence of alpha-synuclein and differing in increments of a small number of amino acids (e.g., 3 amino acids). The peptides are immobilized within the wells of a microtiter dish. Immobilization can be effected by biotinylating one terminus of the peptides. Optionally, different samples of the same peptide can be biotinylated at the N and C terminus and immobilized in separate wells for purposes of comparison. Such is particularly useful for identifying end-specific antibodies. An antibody is screened for specific binding to each of the various peptides. The epitope is defined as occurring within a segment of amino acids that is common to all peptides to which the antibody shows specific binding.

II) General Characteristics of Immunoglobulins

The basic antibody structural unit is known to comprise a tetramer of subunits. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 more amino acids. (See generally, Fundamental Immunology, Paul, W., ed., 2nd ed. Raven Press, N.Y., 1989, Ch. 7 (incorporated by reference in its entirety for all purposes).

The variable regions of each light/heavy chain pair form the antibody binding site. Thus, an intact antibody has two binding sites. Except in bifunctional or bispecific antibodies, the two binding sites are the same. The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat, Sequences of Proteins of Immunological Interest (National Institutes of Health, Bethesda, Md., 1987 and 1991); Chothia & Lesk, J. Mol. Biol. 196:901-917 (1987); or Chothia et al., Nature 342:878-883 (1989).

A. Production of Nonhuman Antibodies

Mouse or other non-human antibodies can be produced by conventional hybridoma technology. The desired binding specificity can be imparted by selection of the immunogen and/or the screening approach. For generating antibodies with an epitope specificity between residues 40 and 55, a fragment of alpha-synuclein consisting of these residues (i.e., 40-55) can be used an immunogen or a longer fragment including these residues up to full-length alpha-synuclein. Antibodies can be screened by binding to overlapping peptides as described above. For producing an antibody preferentially binding to alpha-synuclein, full length alpha-synuclein or a fragment thereof including sufficient residues to constitute an epitope (e.g., 3-15 contiguous residues) can be used as the immunogen.

Chimeric and humanized antibodies have the same or similar binding specificity and affinity as a mouse or other nonhuman antibody that provides the starting material for construction of a chimeric or humanized antibody. Chimeric antibodies are antibodies whose light and heavy chain genes have been constructed, typically by genetic engineering, from immunoglobulin gene segments belonging to different species. For example, DNA encoding the variable domains of a mouse antibody can be sequenced, and DNA construct(s) encoding the variable domains joined to human constant (C) segments, such as IgG1 and IgG4 constructed. The constructs are then expressed to produce the antibody Human isotype IgG1 is preferred. In some methods, the isotype of the antibody is human IgG1. IgM antibodies can also be used in some methods. A typical chimeric antibody is thus a hybrid protein consisting of the V or antigen-binding domain from a mouse antibody and the C or effector domain from a human antibody.

Humanized antibodies have variable region framework residues substantially from a human antibody or consensus of human antibodies (termed an acceptor antibody) and some and usually all six complementarity determining regions substantially or entirely from a mouse-antibody, (referred to as the donor immunoglobulin). See, Queen et al., Proc. Natl. Acad. Sci. USA 86:10029-10033 (1989), WO 90/07861, U.S. Pat. Nos. 5,693,762, 5,693,761, 5,585,089, 5,530,101, and Winter, U.S. Pat. No. 5,225,539 (each of which is incorporated by reference in its entirety for all purposes). The constant region(s), if present, are also substantially or entirely from a human immunoglobulin. The human variable domains are usually chosen from human antibodies whose framework sequences exhibit a high degree of sequence identity with the murine variable region domains from which the CDRs were derived. The heavy and light chain variable region framework residues can be derived from the same or different human antibody sequences. The human antibody sequences can be the sequences of naturally occurring human antibodies or can be consensus sequences of several human antibodies. See Carter et al., WO 92/22653. Certain amino acids from the human variable region framework residues are selected for substitution based on their possible influence on CDR conformation and/or binding to antigen. Investigation of such possible influences is by modeling, examination of the characteristics of the amino acids at particular locations, or empirical observation of the effects of substitution or mutagenesis of particular amino acids.

For example, when an amino acid differs between a murine variable region framework residue and a selected human variable region framework residue, the human framework amino acid should usually be substituted by the equivalent framework amino acid from the mouse antibody when it is reasonably expected that the amino acid: (1) noncovalently binds antigen directly, (2) is adjacent to a CDR region, (3) otherwise interacts with a CDR region (e.g. is within about 6 A of a CDR region), or (4) participates in the VL-VH interface.

Other candidates for substitution are acceptor human framework amino acids that are unusual for a human immunoglobulin at that position. These amino acids can be substituted with amino acids from the equivalent position of the mouse donor antibody or from the equivalent positions of more typical human immunoglobulins. The variable region frameworks of humanized immunoglobulins usually show at least 85% sequence identity to a human variable region framework sequence or consensus of such sequences.

B. Human Antibodies

Human antibodies against alpha-synuclein are provided by a variety of techniques described below. Human antibodies can also be screened for a particular epitope specificity by using only a fragment of alpha-synuclein as the immunogen, and/or by screening antibodies against a collection of deletion mutants of alpha-synuclein. Human antibodies preferably have isotype specificity human IgG1. Several methods are available for producing human antibodies including the trioma method, Oestberg et al., Hybridoma 2:361-367 (1983); Oestberg, U.S. Pat. No. 4,634,664; and Engleman et al., U.S. Pat. No. 4,634,666 (each of which is incorporated by reference in its entirety for all purposes); transgenic non-human mammals described in detail by, e.g., Lonberg et al., WO93/1222, U.S. Pat. Nos. 5,877,397, 5,874,299, 5,814, 318, 5,789,650, 5,770,429, 5,661,016, 5,633,425, 5,625,126, 5,569,825, 5,545,806, Nature 148, 1547-1553 (1994), Nature Biotechnology 14, 826 (1996), Kucherlapati, WO 91/10741 (each of which is incorporated by reference in its entirety for all purposes); and phage display methods See, e.g., Dower et al., WO 91/17271 and McCafferty et al., WO 92/01047, U.S. Pat. Nos. 5,877,218, 5,871,907, 5,858,657, 5,837,242, 5,733,743 and 5,565,332 (each of which is incorporated by reference in its entirety for all purposes).

C. Selection of Constant Region

The heavy and light chain variable regions of chimeric, humanized, or human antibodies can be linked to at least a portion of a human constant region. The heavy chain region can include IgG1, IgG2, IgG3 or IgG4. Light chain constant regions can be lambda or kappa. Antibodies can be expressed as tetramers containing two light and two heavy chains, as separate heavy chains, light chains, as Fab, Fab' F(ab')2, and Fv, or as single chain antibodies in which heavy and light chain variable domains are linked through a spacer.

D. Expression of Recombinant Antibodies

Chimeric, humanized and human antibodies are typically produced by recombinant expression. Recombinant polynucleotide constructs typically include an expression control sequence operably linked to the coding sequences of antibody chains, including naturally associated or heterologous promoter regions. Preferably, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the crossreacting antibodies.

These expression vectors are typically replicable in the host organisms either as episomes or as an integral part of the host chromosomal DNA. Commonly, expression vectors contain selection markers, e.g., ampicillin-resistance or hygromycin-resistance, to permit detection of those cells transformed with the desired DNA sequences.

*E. coli* is one prokaryotic host particularly useful for cloning the DNA sequences of the present invention. Microbes, such as yeast are also useful for expression. *Saccharomyces* is a preferred yeast host, with suitable vectors having expression control sequences, an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

Mammalian cells are a preferred host for expressing nucleotide segments encoding immunoglobulins or fragments thereof. See Winnacker, From Genes to Clones, (VCH Publishers, N Y, 1987). A number of suitable host cell lines capable of secreting intact heterologous proteins have been developed in the art, and include CHO cell lines, various COS cell lines, HeLa cells, L cells, human embryonic kidney cell, and myeloma cell lines. Preferably, the cells are nonhuman. Expression vectors for these cells can include expression control sequences, such as an origin of replication, a promoter, an enhancer (Queen et al., Immunol. Rev. 89:49 (1986)), and necessary processing information sites, such as ribosome binding sites, RNA splice sites, polyadenylation sites, and transcriptional terminator sequences. Preferred expression control sequences are promoters derived from endogenous genes, cytomegalovirus, SV40, adenovirus, bovine papillomavirus, and the like. See Co et al., J. Immunol. 148:1149 (1992).

Alternatively, antibody coding sequences can be incorporated in transgenes for introduction into the genome of a transgenic animal and subsequent expression in the milk of the transgenic animal (see, e.g., U.S. Pat. Nos. 5,741,957, 5,304,489, 5,849,992). Suitable transgenes include coding sequences for light and/or heavy chains in operable linkage with a promoter and enhancer from a mammary gland specific gene, such as casein or beta lactoglobulin.

The vectors containing the DNA segments of interest can be transferred into the host cell by well-known methods, depending on the type of cellular host. For example, calcium chloride transfection is commonly utilized for prokaryotic cells, whereas calcium phosphate treatment, electroporation, lipofection, biolistics or viral-based transfection can be used for other cellular hosts. Other methods used to transform mammalian cells include the use of polybrene, protoplast fusion, liposomes, electroporation, and microinjection (see generally, Sambrook et al., supra). For production of transgenic animals, transgenes can be microinjected into fertilized oocytes, or can be incorporated into the genome of embryonic stem cells, and the nuclei of such cells transferred into enucleated oocytes.

Once expressed, antibodies can be purified according to standard procedures of the art, including HPLC purification, column chromatography, and gel electrophoresis and the like (see generally, Scopes, Protein Purification (Springer-Verlag, NY, 1982).

II. Alpha-Synuclein

Alpha-synuclein was originally identified in human brains as the precursor protein of the non-.beta.-amyloid component of (NAC) of AD plaques. (Ueda et al., Proc. Natl. Acad. Sci. U.S.A. 90 (23):11282-11286 (1993)). Alpha-synuclein, also termed the precursor of the non-Aβ component of AD amyloid (NACP), is a peptide of 140 amino acids. Full-length alpha-synuclein has the amino acid sequence:

```
(Ueda et al., Ibid.; GenBank accession
number: P37840)
                                    (SEQ ID NO: 1)
MDVFMKGLSKAKEGVVAAAEKTKQGVAEAAGKTKEGVLYVGSKTKE

GVVHGVATVAEKTKEQVTNVGGAVVTGVTAVAQKTVEGAGSIAAAT

GFVKKDQLGKNEEGAPQEGILEDMPVDPDNEAYEMPSEEGYQDYEP

EA.
```

Unless otherwise indicated, reference to alpha-synuclein means the natural human amino acid sequence indicated above as well as natural allelic and species variants thereof, including full-length forms and fragments thereof found in samples being analyzed, as well as forms having undergone posttranslational modification, such as phosphorylation. Fragments or variants of alpha-synuclein are numbered as in the exemplified sequences such that aligned residues are allocated the same number.

III. Assays for Secondary Structure Profiles of Alpha-Synuclein

A. The IR Assay

The IR assays of the invention are performed within an apparatus including an infrared source, an infrared sensor element, and an infrared detector. The infrared sensor element is contained within a cell to hold the sample. The cell can be a flow-through cell that allows monitoring the sample continuously.

The infrared source include heat lamps, black body radiators, Nernst lamps, IR-LEDs, and IR-lasers that generate an IR beam.

The infrared sensor element includes an internal reflection element (IRE) transparent to IR radiation and at least one holder. The IRE of the infrared sensor element is typically formed from one or more infrared permeable materials with a high refraction index. These include diamond, germanium, silicon or zinc selenide. For example, the IRE is a germanium crystal. The germanium crystal can be a germanium monocrystal. The IRE can be of trapezoid, parallelogram, fiber, or rod shape. For example, the IRE is of trapezoid or parallelogram shape. For example, the IRE is a germanium crystal with a trapezoid shape. The IRE element is preferably configured by shape, orientation and dimensions to allow for more than one passages of the infrared radiation through IRE, e.g., five passages. The holder is to secure the IRE in the cell. The holder is preferably solid and vertical. Also preferably, there are four holders. It's further preferable that there are four vertical solid holders.

The infrared sensor element is linked to the antibodies discussed above (e.g., 23E8, 1H7, or MJFR1). The antibodies can be linked to the infrared sensor element via a linker, e.g., a silane or thiol linker. The linkers include homogenous silane and thiol linkers, mixtures of silane linkers, and mixtures of thiol linkers. For example, linkers having a chain length of not more than 20 atoms or not more than 15 atoms, are utilized.

Exemplary short chained linkers include silane linkers have one of the following formulas:

$$X_3Si—(CH_2)_n—Y—(CH_2)_{n'}—Z,$$

$$X_2R^1Si—(CH_2)_n—Y—(CH_2)_{n'}—Z \text{ or}$$

$$X(R^1)_2Si—(CH_2)_n—Y—(CH_2)_{n'}—Z,$$

and the thiol linkers have the following formula:

$$HS—(CH_2)_n—Y—(CH_2)_{n'}—Z,$$

wherein X at each occurrence is independently selected from halogen and $C_{1-6}$ alkoxy, n is an integers of 1 to 10, n' is an integer of 1 to 5; $R^1$ at each occurrence is independently selected from $C_{1-6}$ alkyl, Y is selected from a chemical bond, —O—, CO—, —$SO_2$—, —$NR^2$—, —S—, —SS—, —$NR^2CO$—, —$CONR^2$—, —$NR^2SO_2$— and —$SO_2NR^2$— (wherein $R^2$ is H or $C_{1-6}$ alkyl), and Z is an amine-reactive group including —$CO_2H$, —$SO_3H$ and ester derivatives thereof.

$C_{1-6}$ alkyl and $C_{1-6}$ alkoxy includes straight, branched or cyclic alkyl or alkoxy groups having 1 to 6 carbon atoms that may be saturated or unsaturated. In case of cyclic alkyl and alkoxy groups, this refers to those having 3 to 6 carbon atoms. Suitable $C_{1-6}$ alkyl and $C_{1-6}$ alkoxy groups include, among others, methyl and methoxy, ethyl and ethoxy, n-propyl and n-propoxy, iso-propyl and iso-propoxy, cyclopropyl and cyclopropoxy, n-butyl and n-butoxy, tert-butyl and tert-butoxy, cyclobutyl and cyclobutoxy, n-pentyl and n-pentoxy, cyclopentyl and cycloppentoxy, n-hexyl and n-hexoxy, cyclohexyl and cyclohexoxy, and so on. The amine-reactive group Z includes all types of functional groups that are reactive with a free amino group. Among those, —$CO_2H$, —$SO_3H$ and ester derivatives thereof (including active esters) are particularly preferred.

The —$(CH_2)_n$— and —$(CH_2)$ structural elements in the above formulas may also contain one or more double and/or triple bonds and may be substituted with one or more halogen atoms such as fluorine.

In silane linkers, X is independently selected from $C_{1-6}$ alkoxy groups, preferably from methoxy and ethoxy groups. Y is —NHCO—. Z is —$CO_2H$ or an ester derivative thereof, and n is an integer of 1 to 5 and n' is an integer of 1 to 3, preferably n is 3 and n' is 2. The method of preparing the infrared sensor element with short silane linkers comprises activating at least one surface of the internal reflection element by reaction with HF, grafting of the short silane linkers to the activated surface, and covalently coupling the antibody to the internal reflection element via the amine-reactive group of the short silane linkers, and blocking the remaining amine-reactive groups on the short silane linkers with a blocking substance.

In thiol linkers, Y is a chemical bond. Z is —$CO_2H$ or an ester derivative thereof, and n is an integer of 1 to 8 and n' is an integer of 1 to 5, preferably n is 8 and n' is 4. Particularly preferred is a 12-mercaptododecanoic acid NHS ester. The method of preparing the infrared sensor element with short thiol linkers comprises activating at least one surface of the internal reflection element by reaction with HF, grafting of short thiol linkers to the activated surface, and covalently coupling the antibody to the internal reflection element via the amine-reactive group of the short thiol linkers, and blocking remaining amine-reactive groups on the short thiol linkers with a blocking substance.

After linking antibodies to the surface, the surface can be blocked to reduce nonspecific binding to the surface. A detergent-free solution of a globular protein, unreactive with the analyte, but reactive with the silane or thiol linker, is used for chemical quenching/blocking of unspecific binding sites of the sensor element. Suitable blocking substances not cross-reacting with alpha-synuclein includes casein, ethanolamine, L-lysine, polyethylene glycols, albumins, and derivatives thereof, and preferably is casein.

The infrared detector can be a detector acquiring IR absorbance spectrum characterizing a sample in the cell. The two main types of detectors are thermal and photonic (photodetectors). The infrared detector can be, e.g., mercury cadmium telluride (MCT), indium antimonide, indium arsenide, or lead selenide.

The infrared source generates an IR beam. Infrared is denoted as electromagnetic radiation of wavelength greater than that of the red end of the spectrum, having wavelengths of 0.75-1000 μm. Infrared rays are sometimes subdivided into long-wave or far infrared (about 3.0-1000 μm) and short-wave or near infrared (about 0.75-3.0 μm). A wavelength range of about 5.88-6.25 um correspond to the wave number in the part of the infrared spectra including the amide I band of usually 1600-1700 $cm^{-1}$. The reciprocal of the wavelength in reciprocal centimeters, also known as wavenumber, can be used as a measure of the frequency of radiation.

In the assay, the IR beam is submitted to an IR sensor element linked to an antibody bound to alpha-synuclein. The alpha-synuclein absorbs radiation at specific wavelengths, generating an absorbance spectrum, which is captured by an infrared detector. The absorbance spectrum can be represented as a chart showing absorbance at different wavelengths or frequencies of infrared radiation. Such an absorbance spectrum contains several bands corresponding to vibration of different bonds in alpha-synuclein. Amide I and amide II bands are two major bands of the protein infrared absorbance spectrum. The amide I band is of particular interest to the present analysis. An amide I band is a conventional term in biochemical literature to refer to an absorbance due to vibration of the C═O bond in a protein or peptide backbone. The precise frequency or wavelength of the amide I band varies with the type of protein and its aggregation state, typically between 1600 and 1700 $cm^{-1}$. Amide II band results from the N—H bending vibration (40-60%) and from the C—N stretching vibration (18-40%). The amide II band is conformationally sensitive.

For alpha-synuclein in a monomeric state, the band has a peak frequency of approximately 1646 cm$^{-1}$. The frequency of the peak is shifted lower as the alpha-synuclein aggregates. The intensity of the absorbance signals allows for the quantitative or qualitative interpretation of the substance concentration. When analyzing the shift of an amide I band maximum frequency of alpha-synuclein to determine the secondary structure of alpha-synuclein, an amide I band maximum frequency of 1646 cm$^{-1}$ indicates monomeric alpha-synuclein and a lower amide I band maximum frequency of alpha-synuclein indicates aggregated alpha-synuclein.

The amide I band of the determined IR spectrum may have a single peak, the frequency of which provides a value representative of the aggregated state of alpha-synuclein. For example, if the band has a single peak occurring at 1646 cm$^{-1}$, the sample contains alpha-synuclein in a substantially monomeric state. If the single peak shifts down to 1643 cm$^{-1}$ or lower, there is substantial aggregation as occurs in subjects with Lewy body disease. The lower the peak shifts, the greater the proportion and/or extent of aggregated alpha-synuclein. The frequency can range, for example, from about 1646 to 1636, but is often within a range of 1646-1638 or 1646-1640 or 1646-1641 or 1646-1642 or 1646-1643 cm$^{-1}$.

The amide I band can additionally or alternatively be analyzed by analyzing the area of curve and characterizing the band by the midpoint frequency that bisects the area under the curve. Depending on the symmetry of the band, this midpoint frequency may or may not be the same as the frequency of the band peak. The midpoint frequency bisecting the area under the curve can be used as a measure of the amount and extent of aggregation in similar fashion to the frequency of a single peak.

In some spectra, the amide I band can have multiple peaks corresponding to different conformation states of alpha-synuclein (e.g., monomeric, oligomeric and fibrillar). In such cases, an additional analysis can be formed with which the heights or areas under the curve of the respective peaks are compared to determine proportions of the different forms. The IR sensor element can be designed for a parallel detection of at least two wavelength ranges with at least two distinct, but simultaneously applied spectroscopic methods, e.g. infrared absorbance and fluorescence measurements of the analyte. For parallel detection by an additional optical method, the device may further include light source and detector element for such additional optical method, such as light source and detector elements for UV/Vis-fluorescence, at different wavelengths. By detecting UV/Vis-fluorescence, a fluorescence-labeled antibody specifically binding to alpha-synuclein can be used to confirm whether alpha-synuclein binds to a capture antibody linked on the surface of the IR sensor element.

IV. Applications

The methods can be used to diagnose, prognose or monitor subjects, particularly humans, having or at risk of synucleinopathic disease. Synucleinopathic diseases include Parkinson's disease (PD), dementia with Lewy bodies (DLB), the Lewy body variant of Alzheimer's disease (LB-VAD), multiple systems atrophy (MSA), neurodegeneration with brain iron accumulation type-1 (NBIA-1), diffuse Lewy body disease (DLBD), and combined PD and Alzheimer's disease (AD). Suitable patient samples include body fluids, such as blood, CSF, ISF, vitreous humor, saliva, urine, and peritoneal fluid. Tissue samples from the brains of subjects can be subject to similar analyses. However, as obtaining samples from the brains of subject is an undesirably invasive procedure, such analyses are usually confined to cadavers or experimental animal models.

In subjects who are presently asymptomatic, presence of increased amounts of aggregated alpha-synuclein in a body fluid provides an indication of increased risk of development of synucleinopathic disease (e.g., shift of amide I peak below 1646 cm$^{-1}$). In a subject showing some symptoms of a synucleinopathic disease but who has not been diagnosed with the disease, presence of increased amounts of aggregated alpha-synuclein in a body fluid provides an indication the subject has the disease or is at an increased risk of developing in it (e.g., shift of amide I peak at or below a threshold, such as 1643 cm$^{-1}$). In subjects diagnosed with synucleinopathic disease, the level of aggregated alpha-synuclein in a body fluid can be monitored as an indication of the status of the patient, with an increase in aggregated alpha-synuclein over time indicating worsening of the condition (e.g., amide I peak falling further below a threshold, such as 1643 cm$^{-1}$). In a subject diagnosed with a synucleinopathic disease and receiving treatment for it, the level of aggregated alpha-synuclein in a body fluid can provide an indication of response to treatment, with a decrease in the level of aggregated alpha-synuclein indicating the condition of the patient is improving (e.g., amide I peak increasing above a threshold, such as 1643 cm$^{-1}$). The methods can for example be used for patients receiving immunotherapy directed against alpha-synuclein (e.g., an antibody against alpha-synuclein such as PRX-002 or alpha-synuclein fragment that can induce an antibody against alpha-synuclein) or other treatments for synucleinopathic disease.

In any of these methods, the IR spectrum determined from a subject can be compared with IR spectrum from control subjects of known disease or treatment status (e.g., diagnosed with synucleinopathic disease, undergoing positive response to treatment to alpha-synucleinopathic disease).

The methods can also be used for in vitro monitoring of alpha-synuclein in conditioned culture medium from a suitable cell culture can be used for analyzing secondary structure of alpha-synuclein. The application of the IR assay in the cell culture is analogous to that described in a body fluid sample.

Suitable cells include cells transfected with nucleic acids encoding alpha-synuclein, preferably, human alpha-synuclein and cells naturally expressing alpha-synuclein, also preferably human. The alpha-synuclein in transfected cells can bear a mutation, such as S129A, S129D, A53T and A20P. Cells include PeakS cells, SY5Y cells, human cortical cells, human neuroglioma cell lines, neuroblastoma cell lines, human HeLa cells, primary human endothelial cells (e.g. HUVEC cells), primary human fibroblasts or lymphoblasts, primary human mixed brain cells (including neurons, astrocytes, and neuroglia), Chinese hamster ovary (CHO) cells, and the like. SY5Y cells are neuronal cells that can be induced to differentiate by treatment with retinoic acid/BDNF (brain derived neurotrophic factor). Transfected cells expressing pS129 alpha-synuclein at higher levels than normal human cells are preferred.

Monitoring cell culture medium is useful for screening compounds for activity useful in treating synucleinopathic disease. Random libraries of peptides or other compounds can also be screened for suitability. Combinatorial libraries can be produced for many types of compounds that can be synthesized in a step-by-step fashion. Such compounds include polypeptides, beta-turn mimetics, polysaccharides, phospholipids, hormones, prostaglandins, steroids, aromatic compounds, heterocyclic compounds, benzodiazepines, oligomeric N-substituted glycines and oligocarbamates. Large combinatorial libraries of the compounds can be constructed by the encoded synthetic libraries (ESL) method described in Affymax, WO 95/12608, Affymax, WO 93/06121, Columbia University, WO 94/08051, Pharmacopeia, WO 95/35503 and Scripps, WO 95/30642 (each of which is incorporated herein by reference for all purposes). Peptide libraries can also be generated by phage display methods. See, e.g., Devlin, WO 91/18980. The test compounds are typically administered to the culture medium at a concentration in the range from about 1 nM to 1 mM, usually from about 10 µM to 1 mM. Test compounds which are able to inhibit formation, processing or secretion of alpha-synuclein are candidates for further determinations in transgenic animals and eventually human clinical trials.

The methods of the invention can also be used to monitor alpha-synuclein aggregated forms in animal models of synucleinopathic disease. Transgenic animal models of Lewy body disease are described by Masliah, et al. Science 287:1265-1269 (2000); Masliah et al., PNAS USA 98:12245-12250 (2001). Alpha-synuclein can be analyzed either in body fluids as described above for human samples, or in tissue samples taken directly from the animal (see WO 2004/041067 incorporated by reference). Tissue samples can be classified as Lewy body, particulate fraction and soluble fractions.

Although the invention has been described in detail for purposes of clarity of understanding, it will be obvious that certain modifications may be practiced within the scope of the appended claims. All publications and patent documents cited in this application are hereby incorporated by reference in their entirety for all purposes to the same extent as if each were so individually denoted. Unless otherwise apparent from the context any embodiment, aspect, feature or step can be used in combination with any other. If the content associated with a citation or accession number of the like should change with time, the version existing at the effective filing date of this application is intended, the effective filing date being the actual filing date or earlier filing date of a priority application disclosing the citation or accession number.

Examples

Figure 1B:
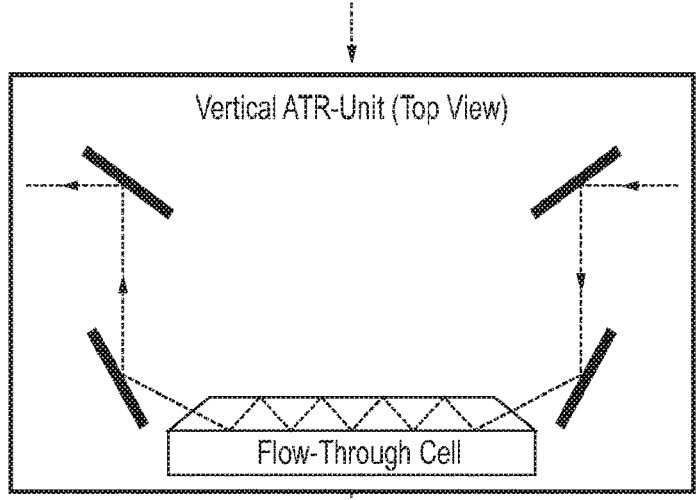
Figure 1C:
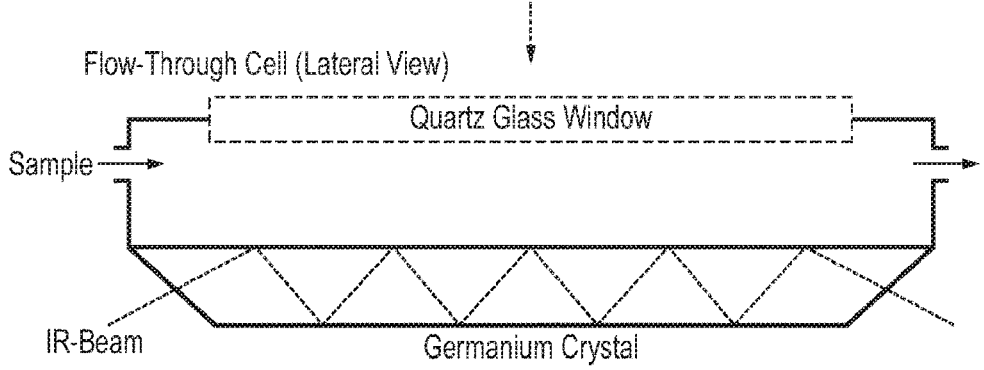
Figure 2:
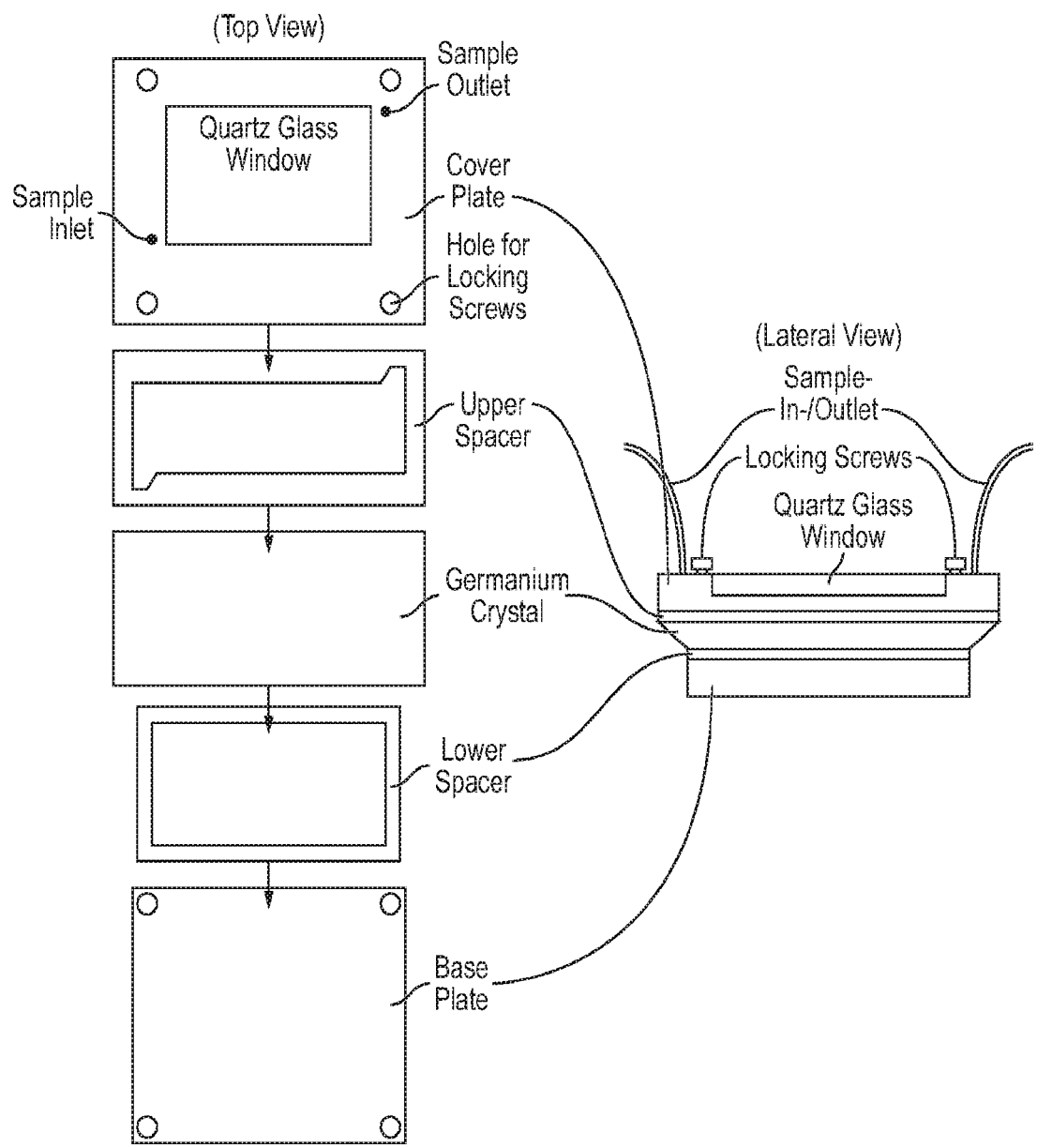
FIG. 2: Optimized flow through cuvette in detail. The device is prepared for a parallel analysis with alternative optical technique via a quartz window in the cover. Gasket elements, Inlet, and outlet ports were optimized regarding stability and flow.
Figure 3:
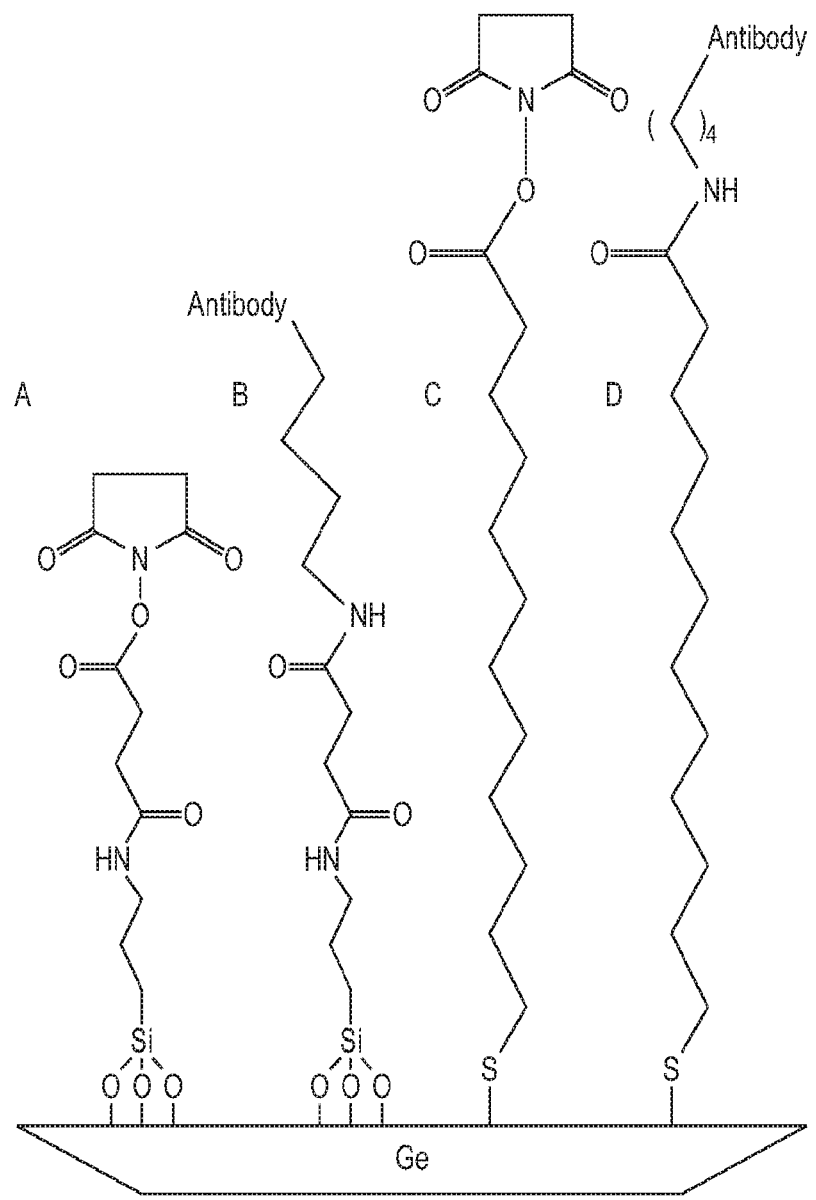
FIG. 3: Short chain triethoxysilane (N-(4,4,4-Triethoxysilanebutyl)succinamic Acid 2,5-Dioxopyrrolidin-1-yl Ester) was covalently attached to germanium (A). The succinimidyl ester reacts with free amines of e.g. proteinogenic lysines, which leads to a stable attachment of the desired protein, e.g., an antibody, of which the attached lysine side chain is shown (B). As alternative linker, 12-mercaptododecanoic acid NHS ester was also covalently attached to germanium_(C). The NHS ester reacts with free amines of e.g., proteinogenic lysines, also forming a covalent bond (D).

An IR-spectrometer equipped with the commercially available sample compartment, "GS11000—25 Reflection Variable Incidence Angle ATR" of Specac (Specac Ltd., Slough, England) (FIG. 1A, optical path FIG. 1B). The optical element, a germanium ATR-crystal (52×20×2 mm, Korth Kristalle GmbH, Altenholz (Kiel), Germany), is enclosed in an optimized bracket (FIG. 1C, FIG. 2). Subsequently specified chemical modifications of the crystal surface generates the specific sensor-property (FIG. 3). Buffers and water are degased in the ultrasonic bath.

Sampling and Pretreatment:

CSF is drawn by lumbal puncture and aliquoted, frozen in liquid nitrogen, shipped and stored at 80° C. Samples are not otherwise pretreated before the measurement, being thawed at 37° C. for 30 seconds and kept on ice until used.

Casein Blocking-Solution:

200 mM sodium hydroxide (NaOH), 1% (w/v) casein from bovine milk (powder), pH adjusted with $H_3PO_4$ to 7.4.

Silanization-Solution:

(N-(4,4,4-triethoxysilanebutyl)succinamic acid 2,5-dioxopyrrolidin-1-yl ester) is synthesized and characterized as described (J. Schartner et al., Journal of the American Chemical Society, 135(10):4079-4087 (2013).

Preparation of the Sensor Surface with Silanes:

The Ge-IRE is bilaterally polished with 0.1 µm grained diamond grinding suspension for 5 min (Struers A/S, Ballerup, Denmark). The crystal is incubated three times in a hydrogen peroxide/oxalic acid mixture (9:1) for 5 mins, rinsed with water between every incubation step and dried with nitrogen gas. Furthermore, the crystal is immediately installed with optimized silicone wavers in the flow-through-cell. The flow-rate is regulated at 1 ml/min by a peristaltic pump (IDEX Health & Science GmbH, Wertheim, Germany). The total-volume of the system amounted to 650 pl.

The sensor surface is incubated with 300 pM silane solution (FIG. 3) in 2-propanol for 60 min, unspecifically linked silane was rinsed with 2-propanol for 30 min. After media change to the reaction buffer, 25 µg/ml antibody solution (1H7, 23E8, or MJFR1) is flushed over the activated silane surface until saturation, monitored by the immobilization kinetics of the amide II band of the antibody. Non-specifically bound antibody is rinsed with PBS-buffer until an equilibrium of the amide II absorbance is achieved. Free reaction sites of the sensor surface are saturated with casein blocking solution followed by rinsing with PBS buffer.

Preparation of the Sensor Surface with Thiols:

The Ge-IRE is prepared similarly as described for silanization (S. M. Han et al., JACS, 123(10):2422-2425 (2001)). After HF treatment, the crystal is immediately immersed into an isopropanol solution containing 1 mM 12-mercaptododecanoic acid NHS ester. The monolayer is assembled after 24 h, the crystal was dried with $N_2$-gas and immediately installed into the ATR set up. Unbound thiols are removed by washing for 30 min with isopropanol. Further preparation is the same as the silanization protocol.

Performing the Measurement:

50 pl csf are added to the PBS-buffered system in a circulating flow. After a binding equilibrium is achieved, unbound material is rinsed with PBS-buffer from the system until no spectral changes were observed. Thus, the absorbance spectrum is calculated from the difference between this state and the casein blocked, PBS rinsed sensor surface. IR-measurements are performed on a Vertex 70V spectrometer (Bruker Optics GmbH, Ettlingen, Germany) equipped with liquid nitrogen cooled mercury-cadmium-telluride (MCT) detector and a vertical variable angle ATR-setup (Specac, Orpington, UK).

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

What is claimed is:

1. A method for determining a profile of secondary structure of alpha-synuclein in a sample, comprising:
   a. introducing the sample into a cell comprising an infrared source, an infrared sensor element linked to an antibody, wherein the antibody is an antibody comprising CDRs H1, H2 and H3 of SEQ ID NOS:12-14 respectively and CDRs L1, L2 and L3 of SEQ ID NOS:15-17 respectively, and an infrared detector, whereby alpha-synuclein in the sample binds to the antibody on the surface of the infrared sensor element;
   b. submitting an infrared beam from the infrared source through the infrared sensor to the infrared detector to obtain an infrared spectrum characterizing the alpha-synuclein of the sample; and
   c. analyzing the obtained infrared spectrum to determine a secondary structure profile of the alpha-synuclein in the sample.

2. The method of claim 1, wherein the secondary structure profile provides an indication of the proportion of alpha-synuclein in aggregated form and/or extent of aggregation of alpha-synuclein in aggregated form.

3. The method of claim 1, wherein step (c) comprises analyzing the shift of an amide I band maximum of alpha-synuclein to determine the secondary structure of alpha-synuclein, an amide I band maximum frequency of 1646 $cm^{-1}$ indicating monomeric alpha-synuclein and a lower amide I band maximum frequency of alpha-synuclein indicating aggregated alpha-synuclein.

4. The method of claim 3, wherein the sample is from a patient with Parkinson's disease, and the amide I band maximum frequency of the sample occurs below 1646 $cm^{-1}$ indicating aggregated alpha-synuclein.

5. The method of claim 4, wherein the patient has prodromal Parkinson's disease.

6. The method of claim 5, wherein the patient has mild Parkinson's disease.

7. The method of claim 5, wherein the patient has moderate Parkinson's disease.

8. The method of claim 5, wherein the patient has advanced Parkinson's disease.

9. The method of claim 1, wherein step (c) comprises comparing the obtained infrared spectrum with a spectrum of alpha-synuclein with a known secondary structure and/or with a known concentration.

10. The method of claim 1, wherein the infrared sensor element comprises a germanium internal reflection element of trapezoid or parallelogram shape transparent in the infrared with sufficient signal to noise ratio to detect an amide I band.

11. The method of claim 1, wherein the antibodies are linked to the infrared sensor by silane or thiol linkers.

12. The method of claim 1, further comprising: (i) detecting a signal, parallel to the infrared analysis, by another optical method, including UV/Vis-fluorescence, at different wavelengths; and/or (ii) combining immuno-ATR-IR vibrational spectroscopy with parallel fluorescence spectroscopy.

13. The method of claim 1, wherein the antibody comprises a mature heavy chain variable region of SEQ ID NO:10 and a mature light chain variable region of SEQ ID NO:11.

14. The method of claim 1, wherein the sample is from a human.

15. The method of claim 14, wherein the human has a Lewy body disease.

16. The method of claim 14, wherein the human has Parkinson's disease.

17. The method of claim 16, wherein the human is receiving immunotherapy for the disease.

18. The method of claim 1, wherein the sample is from a transgenic mouse with a transgene expressing human alpha-synuclein.

19. The method of claim 18 performed multiple times on samples from the same human to detect changes in profile over time.

20. The method of claim 1, wherein the sample is a body fluid.

21. The method of claim 20, wherein the sample is cerebrospinal fluid (CSF) or blood of a human.

22. The method of claim 1, wherein the sample is a brain homogenate of a human or transgenic animal.

23. The method of claim 22, wherein the human is receiving a regime of immunotherapy and the method further comprises changing the regime in response to changes in the profile over time.

24. The method of claim 1, wherein the sample is a medium used to culture cells wherein the cells express recombinant human alpha-synuclein.

25. The method of claim 1, performed on a population of subjects, wherein a greater proportion of subjects with a level of the amide I band maximum frequency of alpha-synuclein below a threshold receive treatment for Parkinson's disease than subjects in which the level of the amide I band maximum frequency of alpha-synuclein is above the threshold.

26. The method of claim 25, the threshold of the amide I band maximum frequency is 1643 $cm^{-1}$.

* * * * *